United States Patent
Ellis et al.

(10) Patent No.: US 6,818,900 B2
(45) Date of Patent: Nov. 16, 2004

(54) OPTICAL RADIATION SENSOR SYSTEM AND METHOD FOR MEASURING RADIATION TRANSMITTANCE OF A FLUID

(75) Inventors: James W. Ellis, London (CA); Mike Sasges, London (CA); Peter Van Doodewaard, St. Thomas (CA); Alex Verdun, London (CA)

(73) Assignee: Trojan Technologies Inc. (CA)

( * ) Notice: Subject to any disclaimer, the term of this patent is extended or adjusted under 35 U.S.C. 154(b) by 0 days.

(21) Appl. No.: 09/882,297

(22) Filed: Jun. 18, 2001

(65) Prior Publication Data

US 2002/0036274 A1 Mar. 28, 2002

Related U.S. Application Data

(60) Provisional application No. 60/211,971, filed on Jun. 16, 2000.

(51) Int. Cl.[7] .................................................. G21G 4/00
(52) U.S. Cl. ..................................... 250/372; 250/493.1
(58) Field of Search ............................. 250/372, 493.1, 250/559; 356/73, 341, 375, 381, 339

(56) References Cited

U.S. PATENT DOCUMENTS

| | | | | | |
|---|---|---|---|---|---|
| 3,655,979 A | * | 4/1972 | Jernigan, Jr. | .................. | 378/55 |
| 4,290,695 A | * | 9/1981 | Schmitt | ........................ | 356/73 |
| 4,358,960 A | * | 11/1982 | Porter | .......................... | 73/705 |
| 4,602,162 A | | 7/1986 | Sperry, III et al. | .......... | 250/436 |
| 5,242,602 A | * | 9/1993 | Richardson et al. | ......... | 210/745 |
| 2001/0046461 A1 | * | 11/2001 | Hamilton | .................... | 422/200 |

FOREIGN PATENT DOCUMENTS

| | | | | | |
|---|---|---|---|---|---|
| EP | 1130381 A1 | * | 9/2001 | .......... | G01N/21/53 |
| NL | 1 003 961 C | | 3/1998 | .......... | G01N/21/59 |

OTHER PUBLICATIONS

Patent Abstracts of Japan, vol. 1998, No. 8, Jun. 30, 1998and JP 10 057954 (Nippon Photo SCI:KK), abstract.

* cited by examiner

*Primary Examiner*—Constantine Hannaher
*Assistant Examiner*—Otilia Gabor
(74) *Attorney, Agent, or Firm*—Katten Muchin Zavis Rosenman

(57) ABSTRACT

An optical radiation sensor device for detecting radiation in a radiation field having a thickness. A preferred embodiment of the device includes a radiation source and a radiation sensor element positioned to receive radiation from the radiation source. A motor (or other motive means) is provided to alter the thickness of the radiation field from a first thickness to a second thickness. The sensor element is capable of detecting and responding to incident radiation from radiation source at the first thickness and at the second thickness. The optical radiation sensor device allows for determination of radiation (preferably ultraviolet radiation) transmittance of a fluid of interest.

20 Claims, 7 Drawing Sheets

OPTICAL RADIATION SENSOR SYSTEM AND METHOD FOR MEASURING RADIATION TRANSMITTANCE OF A FLUID

CROSS-REFERENCE TO RELATED APPLICATION

The present application claims the benefit under 35 U.S.C. §119(e) of provisional patent application Ser. No. 60/211,971, filed Jun. 16, 2000, the contents of which are hereby incorporated by reference.

BACKGROUND OF THE INVENTION

1. Field of the Invention

In one of its aspects, the present invention relates to an optical radiation sensor system. In another of its aspects, the present invention relates to a method for measuring radiation transmittance of a fluid.

2. Description of the Prior Art

Optical radiation sensors are known and find widespread use in a number of applications. One of the principal applications of optical radiation sensors is in the field of ultraviolet radiation fluid disinfection systems.

It is known that the irradiation of water with ultraviolet light will disinfect the water by inactivation of microorganisms in the water, provided the irradiance and exposure duration are above a minimum "dose" level (often measured in units of milliWatt seconds per square centimeter or mW·s/cm$^2$). Ultraviolet water disinfection units such as those commercially available from Trojan Technologies Inc. under the tradenames Trojan UVMax™, Trojan UVSwift™ and Trojan UVLogic™, employ this principle to disinfect water for human consumption. Generally, water to be disinfected passes through a pressurized stainless steel cylinder which is flooded with ultraviolet radiation. Large scale municipal waste water treatment equipment such as that commercially available from Trojan Technologies Inc. under the tradenames UV3000 and UV4000, employ the same principal to disinfect waste water. Generally, the practical applications of these treatment systems relates to submersion of a treatment module or system in an open channel wherein the wastewater is exposed to radiation as it flows past the lamps. For further discussion of fluid disinfection systems employing ultraviolet radiation, see any one of the following:

U.S. Pat. No. 4,482,809,
U.S. Pat. No. 4,872,980,
U.S. Pat. No. 5,006,244,
U.S. Pat. No. 5,418,370,
U.S. Pat. No. 5,539,210, and
U.S. Pat. No. Re36,896.

In many applications, it is desirable to monitor the level of ultraviolet radiation present within the water (or other fluid) under treatment or other investigation. In this way, it is possible to assess, on a continuous or semi-continuous basis, the level of ultraviolet radiation, and thus the overall effectiveness and efficiency of the disinfection process.

It is known in the art to monitor the ultraviolet radiation level by deploying one or more passive sensor devices near the operating lamps in specific locations and orientations which are remote from the operating lamps. These passive sensor devices may be photodiodes, photoresistors or other devices that respond to the impingent of the particular radiation wavelength or range of radiation wavelengths of interest by producing a repeatable signal level (e.g., in volts or amperes) on output leads.

In most commercial ultraviolet water disinfection systems, the single largest operating cost relates to the cost of electricity to power the ultraviolet radiation lamps. In a case where the transmittance of the fluid varies from time to time, it would be very desirable to have a convenient means by which fluid transmittance could be measured for the fluid being treated by the system (or the fluid being otherwise investigated) at a given time. If it is found that fluid transmittance is relatively high, it might be possible to reduce power consumption in the lamps by reducing the output thereof. In this way, the significant savings in power costs would be possible.

The measurement of fluid transmittance is desirable since measurement of intensity alone is not sufficient to characterize the entire radiation field—i.e., it is not possible to separate the linear effects of lamp aging and fouling from exponential effects of transmittance. Further, dose delivery is a function of the entire radiation field, since not all fluid takes the same path.

The prior art has endeavoured to develop reliable radiation (particularly UV) transmittance measuring devices.

For example, it is known to use a single measurement approach. Unfortunately, the single measurement distance requires re-calibration with fluid of known transmittance to account for fouling.

It is also known to use a two-sensor system in which a first sensor is disposed in air and a second sensor is disposed in water. The problem with this approach is that it results in different fouling of each sensor with resulting errors.

Further, some systems require obtaining a sample from a channel of flowing fluid and thereafter measuring the radiation transmittance of the sample. Unfortunately, this approach necessitates the use of additional fluid handling measures which can lead to non-representative samples.

Thus, despite the advances made in the art, there exists a need for an improved device which can measure radiation transmittance of a fluid. Ideally, the device would have one or more of the following characteristics: it would be of simple construction, it would be submersible, it would require only a single sensor and it could be implemented to measure UV transmittance of a fluid in an on-line or random measurement manner.

SUMMARY OF THE INVENTION

It is an object of the present invention to provide a novel optical sensor device which obviates or mitigates at least one of the above-mentioned disadvantages of the prior art.

It is another object of the present invention to provide a novel radiation source module which obviates or mitigates at least one of the above-mentioned disadvantages of the prior art.

It is another object of the present invention to provide a novel process for measuring the transmittance of a fluid in a radiation field.

Accordingly, in one of its aspects, the present invention provides an optical radiation sensor device for detecting radiation in a radiation field having a thickness, the device comprising:

a radiation source;
a radiation sensor element positioned to receive radiation from the radiation source; and
motive means to alter the thickness of the radiation field from a first thickness to a second thickness;
the sensor element capable of detecting and responding to incident radiation from radiation source at the first thickness and at the second thickness.

In another of its aspects, the present invention provides a process for measuring transmittance of a fluid in a radiation field, the process comprising the steps of:

(i) positioning a radiation source and a radiation sensor element in a spaced relationship to define a first thickness of fluid in the radiation field;

(ii) detecting a first radiation intensity corresponding to radiation received by the sensor element at the first thickness;

(iii) altering the first thickness to define a second thickness;

(iv) detecting a second radiation intensity corresponding to radiation received by the sensor element at the second thickness; and (v) calculating radiation transmittance of the fluid in the radiation field from the first radiation intensity and the second radiation intensity.

In another of its aspects, the present invention provides an optical radiation sensor device for detecting radiation in a radiation field generated in a fluid of interest, the device comprising:

a radiation source submersible in the fluid of interest;

a submersible first radiation sensor element positioned in the fluid of interest at a first distance from the radiation source; and a submersible second radiation sensor element positioned in the fluid of interest at a second distance from the radiation source;

wherein: (i) the first distance is different from the second distance, (ii) the first radiation sensor element is capable of detecting and responding to incident radiation from radiation source at the first distance, and (iii) the second radiation sensor element is capable of detecting and responding to incident radiation from radiation source at the second distance.

Thus, the present inventors have discovered a novel optical sensor device which, in a preferred embodiment is simplified in construction in that it only requires a single lamp and single sensor element. The sensor element and radiation source (preferably an ultraviolet radiation lamp) are arranged to create a fluid layer therebetween. By altering the thickness of the fluid layer, it is possible to take multiple (i.e., two or more) radiation intensity readings at multiple, known fluid layer thicknesses. Once these are achieved, using conventional calculations, it is possible to readily calculate the radiation transmittance of the fluid. A process for measuring transmittance of a fluid is also described for implementation of the present optical radiation sensor device. Other advantages will become apparent to those of skill in the art.

BRIEF DESCRIPTION OF THE DRAWINGS

Embodiments of the present invention will be described with reference to the accompanying drawings, wherein like numerals designate like elements, and in which.

DETAILED DESCRIPTION OF THE PREFERRED EMBODIMENTS

Figure 1:
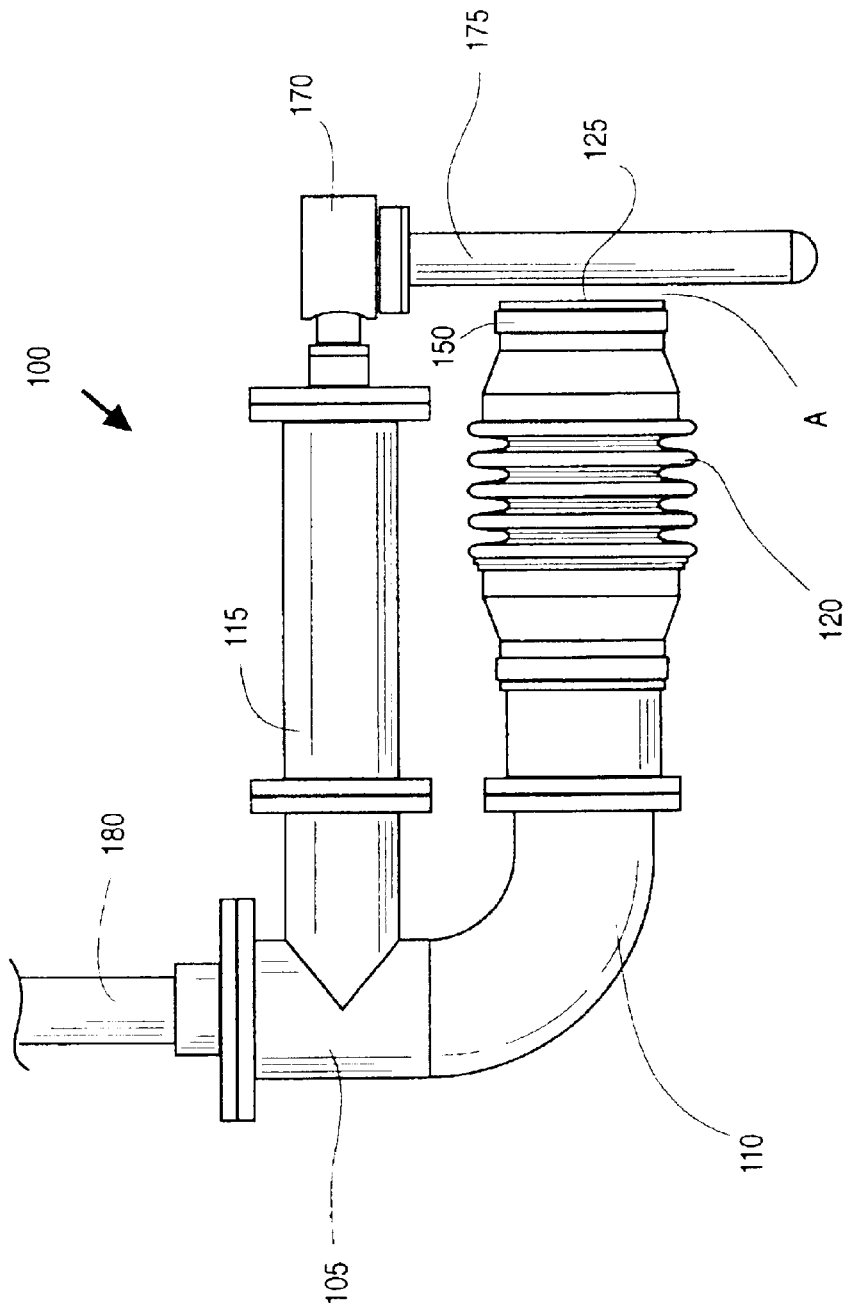
FIG. 1 illustrates a side elevation view of an embodiment of the present optical radiation sensor device.
Figure 2:
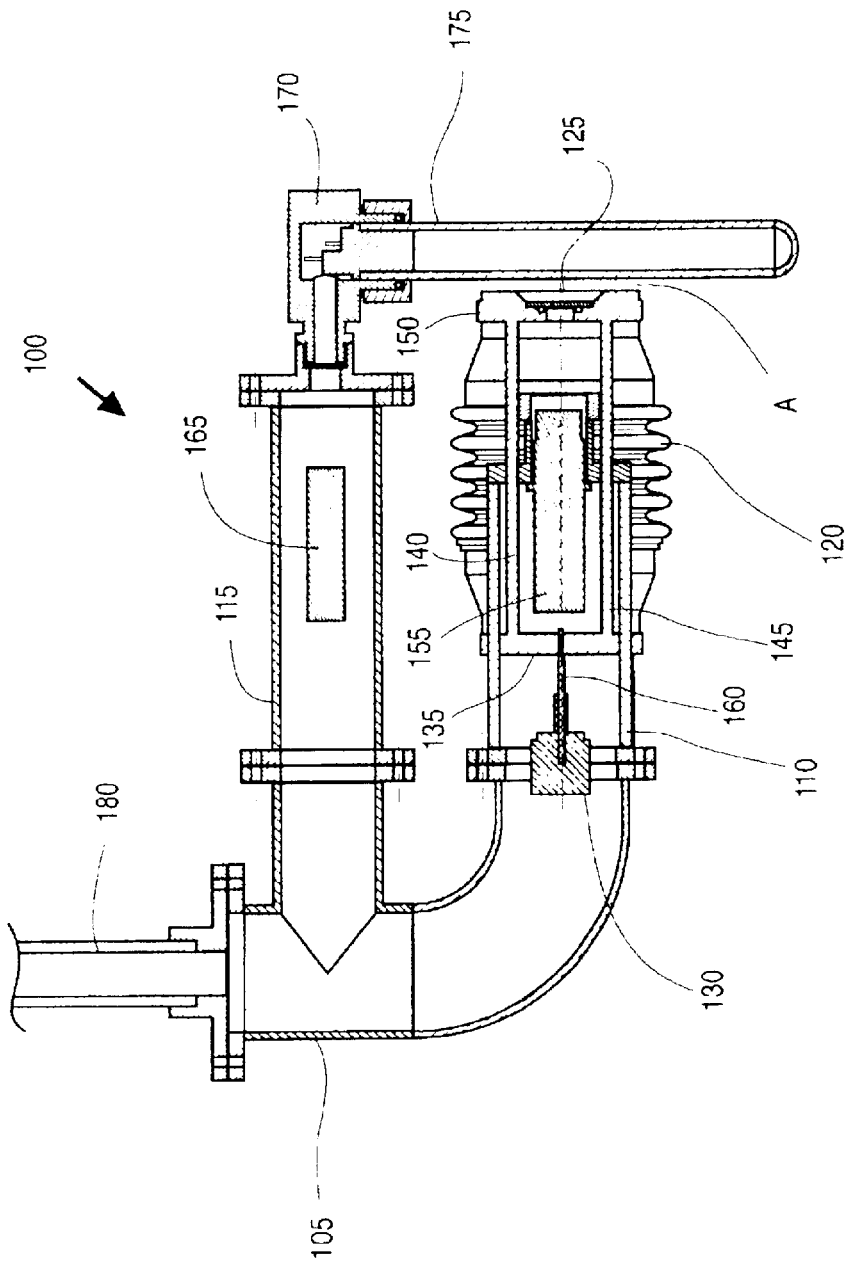
FIG. 2 illustrates a cross-sectional view of the device illustrated in FIG. 1.

With reference to FIGS. 1 and 2, there is illustrated an optical radiation sensor device 100. Sensor device 100 comprises a fluid tight housing 105 which comprises a sensor housing 110 and a radiation source housing 115.

Sensor housing 110 has attached to a terminal portion thereof a boot 120. Boot 120 can be made of any suitable flexible material which is fluid tight and can withstand the rigours of the radiation environment in which it is used. For example, boot 120 may be constructed of Neoprene™, Viton™ and the like. Boot 120 may be sealably attached to the terminal end of sensor housing 110 in any conventional manner (not shown). Disposed at the distal end of boot 120 is a radiation transparent window 125.

Disposed within sensor housing 110 is a motor 130. Also disposed within sensor housing 110 is a slidable first disk 135 which is connected to a pair of rods 140,145. Rods 140,145 are, in turn, connected a second disk 150 having disposed therein radiation transparent window 125. Disposed between rods 140,145 is an optical sensor 155 which contains a photodiode (not shown) or other radiation sensor material. The sensor itself may be chosen from conventional sensors. For example, a suitable sensor is commercially available from IFW (Germany).

As illustrated, a screw rod 160 interconnects motor 130 and first disk 135.

Disposed within radiation source housing 115 is a ballast 165 conventionally used to control a radiation source such as an ultraviolet lamp.

A connection block 170 is connected to the distal end of radiation source housing 115 in a fluid tight manner.

A radiation source 175 emanates from and is in a fluid tight engagement with connection block 170. Radiation source 175 is conventional. Preferably, radiation source 175 is an ultraviolet radiation lamp, more preferably such a lamp encased in a radiation transparent protective sleeve (e.g., a sleeve made of quartz).

As will be apparent and appreciated by those of skill in the art, it is conventional to have a electrical leads emanating from motor 130, optical sensor 155 and ballast 165 through sensor housing 110 and radiation source housing 115, respectively, and then through a fluid tight conduit 180. For clarity and understanding the illustrated embodiment, the electrical leads have not been shown. Thus, those of skill in the art will recognize that illustrated optical radiation sensor device 100 is designed to be entirely submersible in the fluid of interest.

As will be apparent, fluid passing through optical sensor device 100 will, at least in part, pass through a gap A created between second disk 150 and radiation source 175. In other places in the specification, this gap is referred to as a fluid layer, particularly a fluid layer having a specific thickness.

The fluid layer thickness between disk 150 and radiation source 175 may be altered in the following manner. Motor 130 is actuated thereby actuating screw rod 160 which will serve to retract first disk 135 and rods 140,145 into sensor housing 110. This has the effect of increasing the thickness of gap A between second disk 150 and radiation source 175 or, in other words, increasing the thickness of the fluid layer.

Through the use of conventional stepper motors, position sensors, mechanical constraints (e.g., fixture travel means such as a solenoid, a cam, a crank shaft, physical stops and other relatively simple mechanical constructions) or the like, it is possible to take measurements of the radiation intensity detected by sensor 155 at various, known values for gap A. Once various intensities at various gaps are known, the radiation transmittance of fluid passing through optical radiation sensor device 100 may be readily determined as will be explained hereinbelow.

As will be appreciated by those with skill in the art, in the embodiment illustrated in FIGS. 1 and 2, sensor 155 and radiation source 175 are stationary. Specifically, the fluid layer thickness is altered by movement of second disk 150 with respect to radiation source 175.

Figure 3:
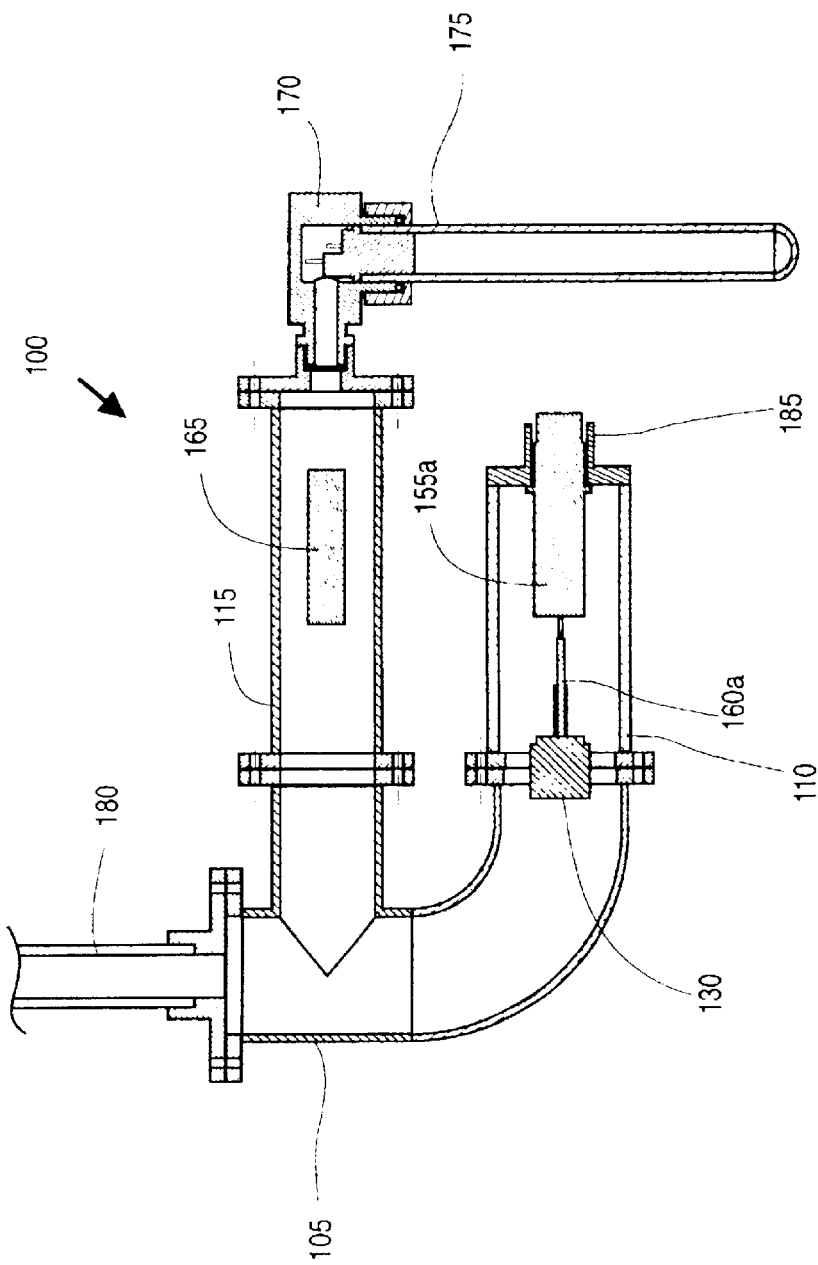
FIG. 3 illustrates an alternate embodiment of the optical radiation sensor device illustrated in FIG. 2.
Figure 4:
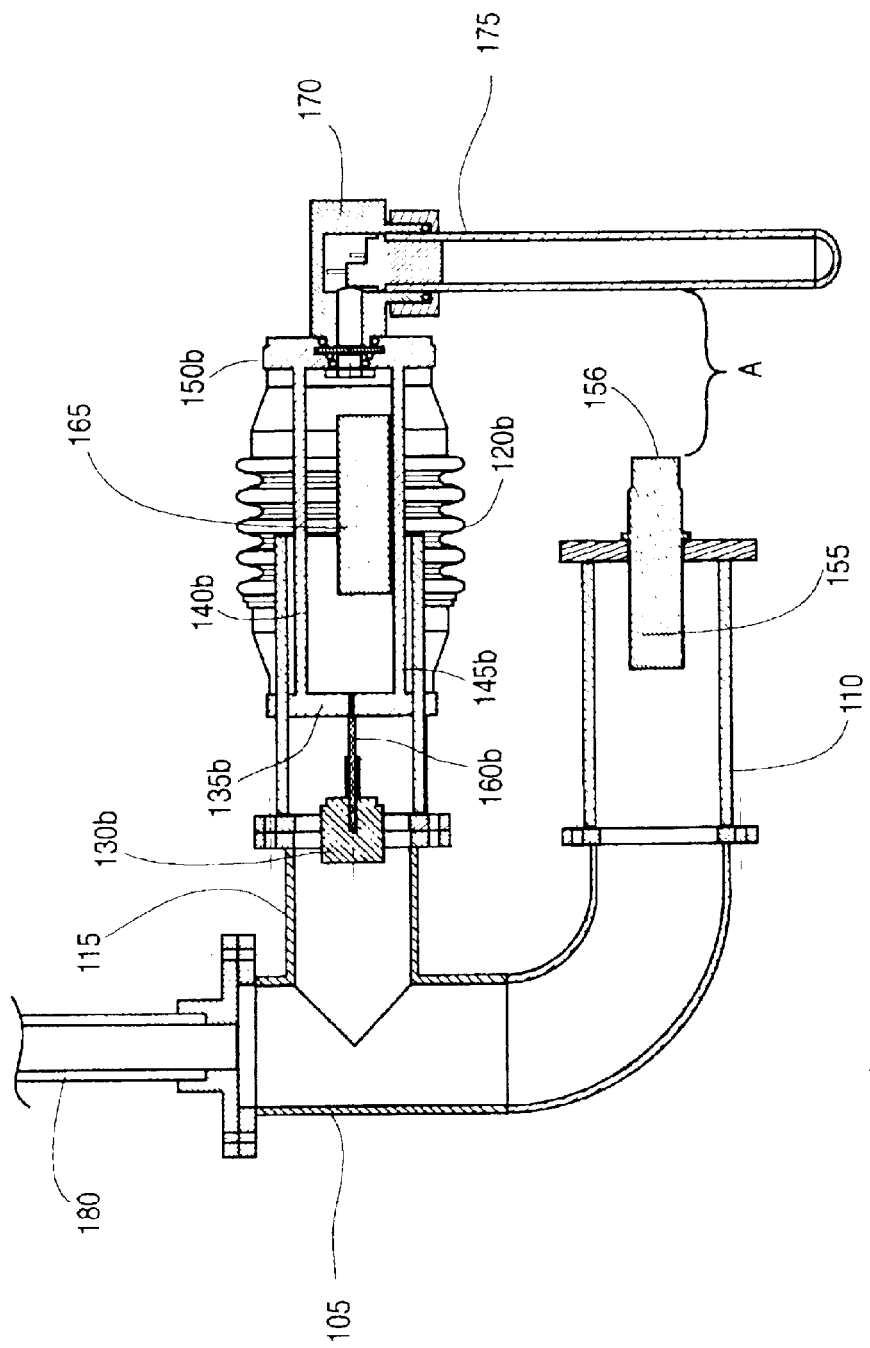
FIG. 4 illustrates a further alternate embodiment to the optical radiation sensor device illustrated in FIG. 2.

FIGS. 3 and 4 illustrate alternate embodiments for varying the thickness of the fluid layer. In FIGS. 1–4, like reference numerals designate like elements. In FIG. 3, the reference numerals for elements which have been moved and/or modified from FIG. 1 carry the suffix "a". Similarly, in FIG. 4, the reference numerals for elements which have been moved and/or modified from FIG. 1 carry the suffix "b".

With reference to FIG. 3, it will be seen that the distal end of sensor housing 110 has been modified to include a body 185 within which sensor 155a is movable. Movement of sensor 155a may be accomplished by placing a motor 130a which is interconnected to sensor 155a via a screw rod 160a. When it is desired to alter the thickness of the fluid layer, motor 130a is actuated thereby actuating screw rod 160a which, depending on the rotation of screw rod 160a, will result in sensor 155a being moved toward or away from radiation source 175.

With reference to FIG. 4, there is illustrated yet another embodiment for altering the thickness of the fluid layer referred to above. In this case, radiation sensor 155 having a face 156 is stationary and radiation source 175 may be moved thereby altering the thickness of the fluid layer between sensor 155 and radiation source 175. Movement of radiation source 175 may be accomplished by placing a motor 130b which is interconnected to a connection block 170 via a screw rod 160b. The thickness of the fluid layer between face 156 and radiation source 175 may be altered in the following manner. Motor 130b is actuated thereby actuating screw rod 160b which, depending on the rotation of screw rod 160b, will serve to: (i) retract radiation source 175 and rods 140b, 145b into radiation source housing 115, or (ii) extend radiation source 175 and rods 140b, 145b from radiation source housing. This has the effect of increasing the thickness of gap A between face 156 and radiation source 175 or, in other words, increasing the thickness of the fluid layer.

Figure 5:
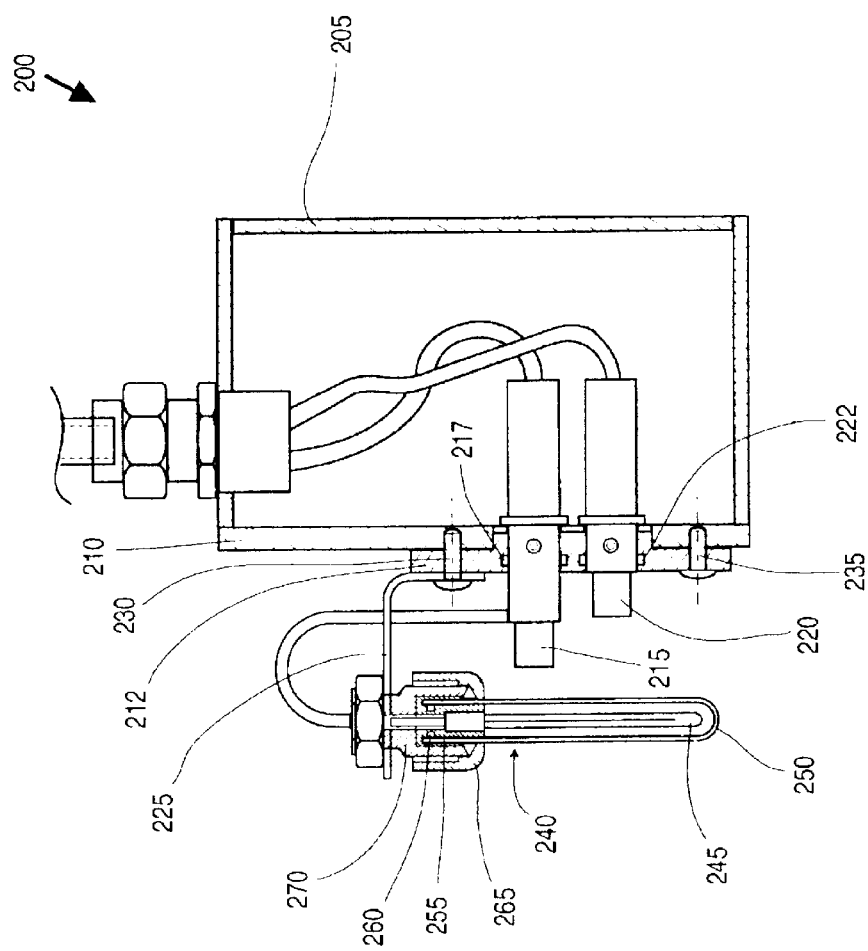
FIG. 5 illustrates a cross-sectional view of an alternate embodiment of the present optical radiation sensor device.

With reference to FIG. 5, there is illustrated an optical radiation sensor device 200 which is an alternate embodiment of the present optical radiation sensor device.

Thus, device 200 comprises a housing 205 which is substantially fluid-tight. Housing 205 comprises a wall 210 having attached thereto a plate 212. Disposed in plate 212 is a first radiation sensor 215 and a second radiation sensor 220. Radiation sensor 215 is maintained in fluid tight engagement with plate 212 via an O-ring 217. Radiation sensor 220 is maintained in fluid tight engagement with plate 212 via an O-ring 222.

A bracket 225 is attached to plate 212 and wall 210 via a bolt 230. A bolt 235 serves to further secure plate 212 to wall 210.

Attached to bracket 225 is a radiation source assembly 240. Radiation source assembly 240 comprises a radiation source 245 disposed within a radiation transparent protective sleeve 250. As illustrated, protective sleeve 250 is closed at one end and opened at the other. Disposed in the open end of protective sleeve 250 is a plug 255 against which the open end of protective sleeve 250 abuts. An O-ring 260 is provided in plug 255 a coupling nut 265 and a sleeve 270 are in threaded (or other) engagement such that when coupling nut 265 is tightened, sleeve 270 is biassed against plug 255 which serves to compress O-ring 260 thereby creating a fluid-tight arrangement.

As illustrated in FIG. 5, first sensor 215 and second sensor 220 have respective faces which are disposed at different distances from radiation source assembly 240. As will be understood by those of skill in the art, the sensor elements (not shown) disposed with in each of first sensor 215 and second sensor 220 my be detecting radiation at the same or different distance—i.e., it is difference in the respective fluid layer thickness between radiation source 245 and first sensor 215 and between radiation source 245 and second sensor 220 which is important. Thus, device 200 is able to feed back radiation intensity readings at two distances from the radiation source.

Figure 6:
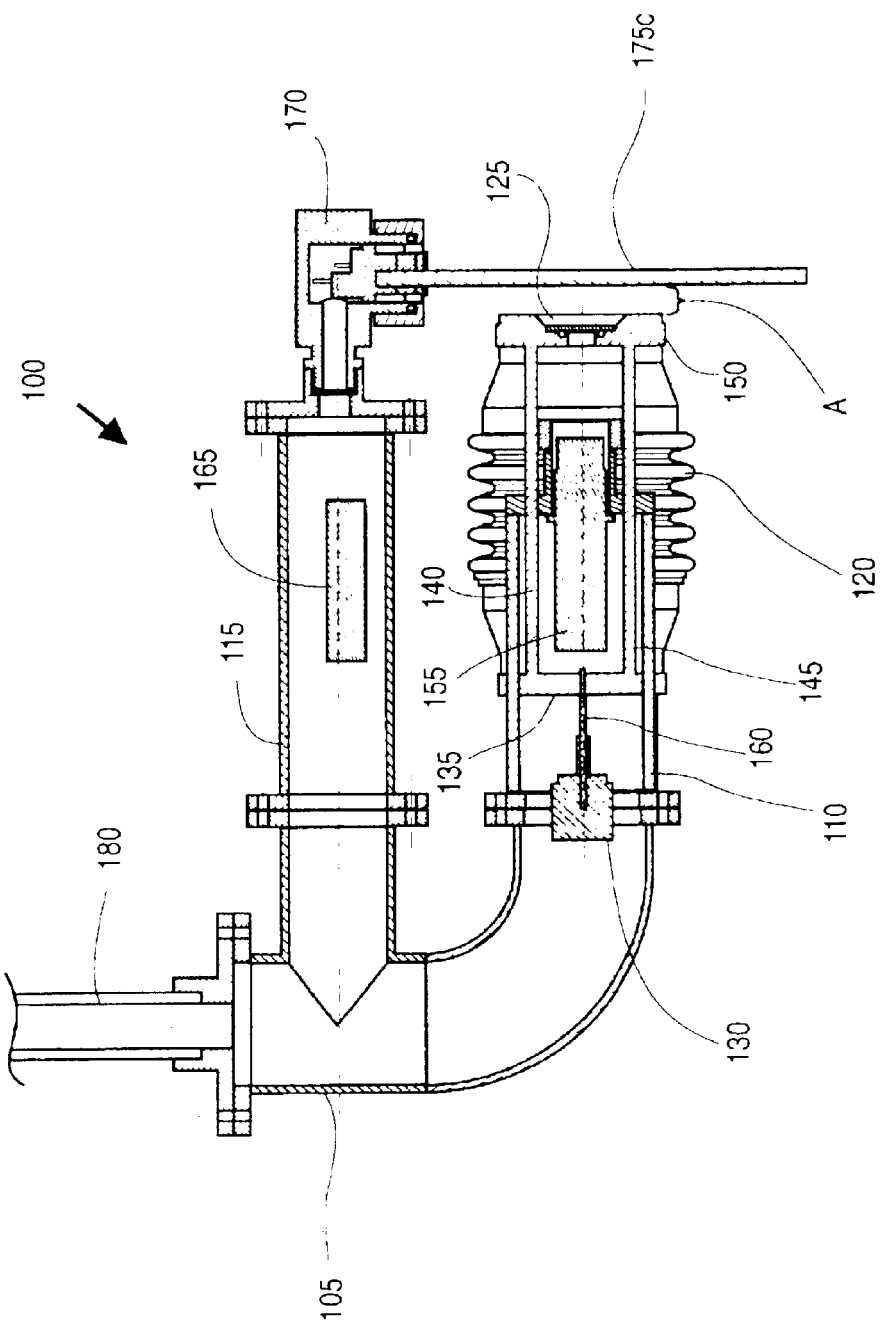
FIG. 6 illustrates yet a further alternate embodiment of the optical radiation sensor device illustrated in FIG. 2.

FIG. 6 illustrates yet a further alternate embodiment to the device illustrated in FIG. 2 for varying the thickness of the fluid layer. In FIGS. 2 and 6, like reference numerals designate like elements. In FIG. 6, the reference numerals for elements which have been moved and/or modified from FIG. 2 carry the suffix "c".

Thus, with reference to FIG. 6, the principal change to the embodiment illustrated in FIG. 2 is the presence of a flat panel radiation source 175c.

Figure 7:
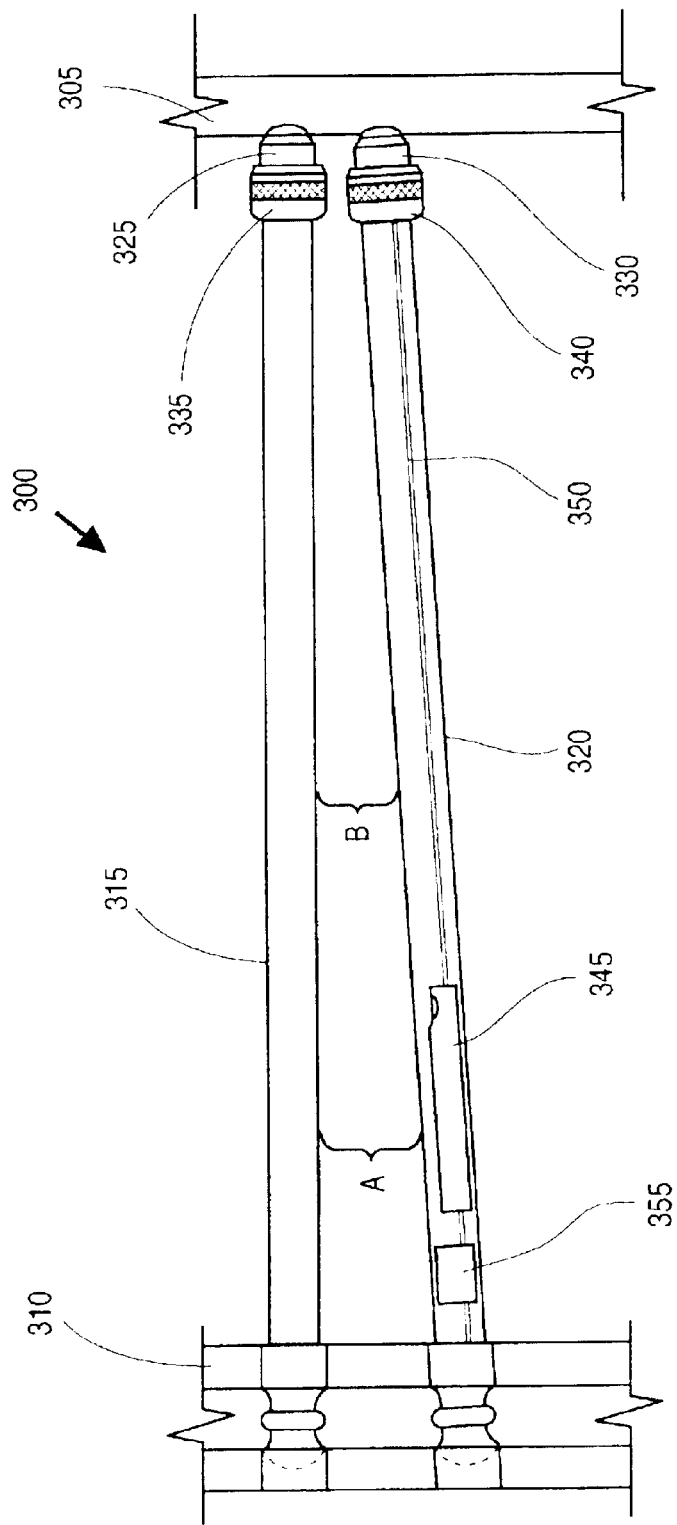
FIG. 7 illustrates yet a further alternate embodiment of the optical radiation sensor device illustrated in FIG. 2.

With reference to FIG. 7, there is illustrated a portion of a radiation source module 300. As will be apparent to those of skill in the art, radiation source module 300 is a of a design similar to that described in any one of U.S. Pat. Nos. 4,482,809, 4,872,980 and 5,006,244 referred to hereinabove. Thus, radiation source module 300 comprises a first support leg 305 and a second support leg 310. In the illustrated embodiment, second support leg 310 comprises a pair of split plates which are held together to surround a portion of a pair of sleeves 315,320. Each of sleeves 315,320 is made of a radiation transparent material such as quartz.

First support leg 305 further comprises a pair of sockets 325,330 welded (or otherwise connected) thereto for receiving the open ends of sleeves 315,320, respectively. A pair of coupling nuts 335,340 are used to connect sleeves 315,320, respectively, to sockets 325,330, respectively, in a substantially fluid-tight manner. The specific design and sealing mechanisms are set out in various of the patents referred to above and thus, are within the perview of a person skilled in the art.

Disposed within sleeve 315 is a radiation source (not shown) such as an ultraviolet lamp. The electrical leads for the radiation source disposed within sleeve 315 are fed through socket 325 and support leg 305 to a source of electricity (not shown).

Sleeve 320 comprises a radiation sensor 345 which is capable of being moved within sleeve 320 along a guide 350 via a motor 355 or other suitable motive means.

As illustrated in FIG. 7, sleeves 315,320 are in a skewed or substantially non-parallel relationship with respect to each other. Thus, in this relationship, it would be apparent that, when sensor 345 is moved along guide 350, the fluid layer thickness between sensor 345 and sleeve 315 (and thus the distance from sensor 345 to the radiation source disposed within sleeve 315) can be varied, for example between a first fluid layer thickness A and a second fluid layer thickness B. Thus, in this embodiment, motor 355 (or other suitable motive means) alters the fluid layer thickness between the radiation source and the radiation sensor by moving the latter longitudinally with respect to the former in a non-parallel manner.

In summary, the embodiment illustrated in FIG. 5 comprises the use of a pair of static sensors whereas the embodiments illustrated in FIGS. 1–4 and 6 and 7 illustrate the use of a single sensor in a dynamic manner. The common feature is that the embodiments illustrated in FIGS. 1–7 provide for obtaining intensity readings from at least two distances from a radiation source in question. These intensity readings each represent a measurement of the radiation detected by a sensor at each (two or more) fluid layer thickness—each thickness is defined by the distance between a sensor and a radiation source. Once this is done, radiation (preferably ultraviolet radiation) transmittance analysis may be achieved as follows.

Consider a system comprising a single lamp and a single sensor. A fluid layer is provided between the lamp and sensor. The lamp has an intensity at its surface of $I_o$. The thickness of the fluid layer is varied from between thickness x and fluid thickness y. These distances are readily determined by feedback from the motor or other motive means, by measurement, by the design of the optical radiation sensor system and/or by the design of the disinfection system.

The sensor optics may be designed to accept radiation from a single known plane or location on a source, which means that all light reaching the sensor has travelled substantially the same distance. It is known that the sensor output, $S_d$, for light arriving from a source through fluid thickness d is given by the equation $$S_d = I_o k_a k_g f_l f_s e^{-kd}$$

where $I_o$ is the intensity at the lamp, $k_a$ is the gain factor of the sensor, $k_g$ is a geometrical factor, $f_l$ is the reduction due to fouling at the lamp sleeve, $f_s$ is the reduction due to fouling at the sensor window, and k is the fluid absorbance with units of 1/distance. The geometrical factor may be held constant through careful design of the sensor window, apertures and lenses.

Taking intensity readings at two fluid thicknesses, x and y, and taking the ratio of these two readings results in the following equation:

$$\frac{S_x}{S_y} = e^{k(y-x)}$$

Note that all factors including lamp output, sensor gain, and fouling have cancelled and do not appear in this equation. The two sensor readings and the fluid thicknesses are known, enabling the calculation of the fluid absorbance or transmittance.

The foregoing discussion is particularly applicable to the case where a single sensor and single lamp is used (e.g., the embodiments of FIGS. 1–4 and 6–7), but is readily adapted to the case where two sensors are used (e.g., the embodiment of FIG. 5) by calculating $S_d$ for each of the two sensors. The reason for this is that lamp output, sensor gain and/or fouling may not cancel as described in the preceding paragraph.

Those of skill in the art will also recognize that the Beer-Lambert law, from which the foregoing discussion derives, may also be written in terms of logarithms in base 10, or directly in terms of transmittance. The general principle behind determining the absorbance or transmittance is the same as described above.

Those skilled in the art will recognize that, for clarity, various simplifications have been made to facilitate clear presentation of the concepts above. Standard modeling and more sophisticated calculation can be used to account for deviations from the ideal described above.

While the present invention has been described with reference to preferred and specifically illustrated embodiments, it will of course be understood by those skilled in the arts that various modifications to these preferred and illustrated embodiments may be made without departing from the spirit and scope of the invention. For example, the present invention has been illustrated with reference to a "stand alone" radiation source module which can be used to measure the radiation (preferably ultraviolet radiation) transmittance of fluid in any radiation treatment module and/or system such as one similar in overall design to those described in U.S. Pat. Nos. 4,872,980, 5,006,244, 5,418,370, 5,539,210 and Re36,896. As such, the "stand alone" radiation source module may be a temporarily or permanently installed in the fluid treatment system. Further, it is, of course, possible to incorporate the approach described above with the specifically illustrated embodiments in an actual radiation source module which forms part of the fluid treatment system such as those described in the above-mentioned United States patents. Still further, it is possible to employ the present optical radiation sensor system in a fluid treatment device such as those commercially available from Trojan under the tradenames Trojan UVMax™, Trojan UVSwift™ and Trojan UVLogic™ etc. Still further, while it is most preferred to use the present invention with respect to treatment of liquids such as water, (i.e., wastewater), it is possible to utilize the present optical radiation sensor system in a gas treatment system. Still further, it may be possible, in some applications to omit a protective sleeve (e.g., made out of quartz) for radiation source 175. Other modifications which do not depart from the spirit and scope of the present invention will be apparent to those with skill in the art.

All publications, patents and patent applications referred to herein are incorporated by reference in their entirety to the same extent as if each individual publication, patent or patent application was specifically and individually indicated to be incorporated by reference in its entirety.

What is claimed is:

1. An optical radiation sensor device for detecting radiation in a radiation field, the device comprising:

a stationary radiation source;

a stationary radiation sensor element positioned to receive radiation from the radiation source;

a boundary element disposed between the radiation source and the radiation sensor element to define a thickness corresponding to the distance between the boundary element and the radiation source; and motive means to alter the relative distance between the boundary element and the radiation source to thereby alter the thickness of the radiation field from a first thickness to a second thickness;

the sensor element capable of detecting and responding to incident radiation from radiation source at the first thickness and at the second thickness.

2. The optical sensor device defined in claim 1, wherein the motive means alters the relative linear distance between the boundary element and the radiation source.

3. The optical sensor device defined in claim 1, wherein the motive means alters the thickness of the radiation field in a step-wise manner.

4. The optical sensor device defined in claim 1, wherein the motive means alters the thickness of the radiation field in a continuous manner.

5. The optical sensor device defined in claim 1, wherein the device is submersible in a fluid of interest.

6. The optical sensor device defined in claim 1, wherein the device is submersible in a liquid of interest.

7. The optical sensor device defined in claim 1, wherein the device is submersible in water.

8. A radiation source module comprising the optical sensor device defined in claim 1.

9. A fluid treatment system comprising the optical sensor device defined in claim 1.

10. A water treatment system comprising the optical sensor device defined in claim 1.

11. A water disinfection system comprising the optical sensor device defined in claim 1.

12. A process for measuring transmittance of a fluid in a radiation field, the process comprising the steps of:
   (i) disposing the optical radiation sensor device defined in claim 1 in the fluid;
   (ii) generating radiation from the radiation source
   (iii) detecting a first radiation intensity corresponding to radiation received by the sensor element at the first thickness;
   (iv) altering the first thickness to define a second thickness;
   (v) detecting a second radiation intensity corresponding to radiation received by the sensor element at the second thickness; and
   (vi) calculating radiation transmittance of the fluid in the radiation field from the first radiation intensity and the second radiation intensity.

13. The process defined in claim 12, wherein Step (iii) comprises altering the relative linear distance between the radiation source and the radiation sensor.

14. The process defined in claim 12, wherein Step (iii) comprises altering the first thickness of the radiation field in a step-wise manner.

15. The process defined in claim 12, wherein Step (iii) comprises altering the first thickness of the radiation field in a continuous manner.

16. An optical radiation sensor device for detecting fluid transmittance in a radiation field generated in a fluid flow of interest, the device comprising:

a radiation source submersible in the fluid flow of interest;

a submersible first radiation sensor element positioned in the fluid flow of interest at a first distance from the radiation source, said first radiation sensor element being configured to measure a first intensity of the radiation field in the fluid flow;

a submersible second radiation sensor element positioned in the fluid flow of interest at a second distance from the radiation source, said second radiation sensor element being configured to measure a second intensity of the radiation field in the fluid flow, said second radiation sensor element being disposed substantially parallel to said first radiation sensor element with respect to a direction of the fluid flow;

structure to use the first intensity and the second intensity to calculate fluid transmittance in the radiation field;

wherein: (i) the first distance is different from the second distance, (ii) the first radiation sensor element is capable of detecting and responding to incident radiation from said radiation source at the first distance, and (iii) the second radiation sensor element is capable of detecting and responding to incident radiation from said radiation source at the second distance.

17. A radiation source module comprising the optical sensor device defined in claim 16.

18. A fluid treatment system comprising the optical sensor device defined in claim 16.

19. A water treatment system comprising the optical sensor device defined in claim 16.

20. A water disinfection system comprising the optical sensor device defined in claim 16.

* * * * *